US011138981B2

(12) United States Patent
Brown et al.

(10) Patent No.: US 11,138,981 B2
(45) Date of Patent: Oct. 5, 2021

(54) SYSTEM AND METHODS FOR MONITORING VOCAL PARAMETERS

(71) Applicant: i2x GmbH, Berlin (DE)

(72) Inventors: Samuel Brown, Berlin (DE); Mehak Khajuria, Parsippany, NJ (US); Michael Brehm, Berlin (DE)

(73) Assignee: I2X GMBH, Berlin (DE)

( * ) Notice: Subject to any disclaimer, the term of this patent is extended or adjusted under 35 U.S.C. 154(b) by 120 days.

(21) Appl. No.: 16/547,339

(22) Filed: Aug. 21, 2019

(65) Prior Publication Data
US 2021/0056976 A1 Feb. 25, 2021

(51) Int. Cl.
G10L 17/22 (2013.01)
G10L 17/06 (2013.01)
G06F 21/32 (2013.01)
G06F 16/683 (2019.01)

(52) U.S. Cl.
CPC ............ G10L 17/22 (2013.01); G06F 16/683 (2019.01); G06F 21/32 (2013.01); G10L 17/06 (2013.01)

(58) Field of Classification Search
CPC ......... G10L 15/00; G10L 17/00; G10L 21/00; G10L 21/003; G10L 25/00; G10L 25/03; G10L 25/51; G10L 25/60; G10L 25/63; G10L 25/90; G10L 2025/906
See application file for complete search history.

(56) References Cited

U.S. PATENT DOCUMENTS

| | | | |
|---|---|---|---|
| 9,666,204 B2* | 5/2017 | Manjunath | G10L 21/003 |
| 10,755,731 B2* | 8/2020 | Suzuki | G10L 15/04 |
| 2015/0280670 A1* | 10/2015 | Kauffmann | G10L 21/034 |
| | | | 381/107 |
| 2017/0195491 A1* | 7/2017 | Odinak | G06Q 10/063112 |
| 2017/0256268 A1* | 9/2017 | Sinder | G10L 17/00 |
| 2017/0364516 A1* | 12/2017 | Shellef | G10L 15/24 |
| 2018/0040325 A1* | 2/2018 | Melanson | G10L 17/00 |
| 2018/0046710 A1* | 2/2018 | Raanani | G06F 16/683 |
| 2018/0061415 A1* | 3/2018 | Penilla | G01C 21/3641 |
| 2018/0122374 A1* | 5/2018 | Bassemir | G10L 25/72 |
| 2018/0130475 A1* | 5/2018 | Page | G06F 21/32 |
| 2019/0130900 A1* | 5/2019 | Tsai | G10L 15/22 |
| 2019/0205329 A1* | 7/2019 | Subramanian | G06Q 30/0269 |
| 2019/0228778 A1* | 7/2019 | Lesso | G10L 17/06 |
| 2020/0228521 A1* | 7/2020 | Edwards | H04W 12/63 |

* cited by examiner

Primary Examiner — Linda Wong
(74) Attorney, Agent, or Firm — Foley & Lardner LLP

(57) ABSTRACT

Systems and methods for detection, classification, and diagnosis of vocal anomalies in vocal streams are disclosed. Discussed are a method for generating a biometric voiceprint for analyzing user vocal streams to detect and classify vocal anomalies and a method for notifying the appropriate party, where the notification is based on the diagnosis reported by the system. Manual classification in the event of automatic classification failure is discussed, where the manual classification data can be used as training data to improve the functionality of the classification model.

20 Claims, 4 Drawing Sheets

SYSTEM AND METHODS FOR MONITORING VOCAL PARAMETERS

FIELD OF THE DISCLOSURE

The present application generally relates to the field of non-intrusive vocal monitoring. More particularly, the present disclosure relates to systems and methods for continuously monitoring vocal parameters in voice communications, and systems and methods for selecting a diagnosis of a vocal anomaly and communicating the cause of the anomaly to another party for the purposes of correction.

BACKGROUND OF THE DISCLOSURE

Clear speech is important for call centers, sales departments, and other fields that depend on frequent vocal communication. If left unaddressed, vocal clarity issues can cause miscommunications or disruption of effective service. Fluctuations in vocal clarity can be difficult to detect and diagnose.

BRIEF SUMMARY OF THE DISCLOSURE

One technical issue addressed by the present disclosure is continuous and non-intrusive vocal monitoring and automatic notifications for remediation of the physiological, physical and mental health of users who spend a considerable amount of time vocally communicating; either as part of their profession or for personal use. This is achieved via establishing a standard biometric voiceprint of a user, configuring a threshold for a typical variation range, and continuously monitoring of the voice of the user. If a parameter of the user's voice exceeds the threshold of the biometric voiceprint, a vocal anomaly has been detected. Once a vocal anomaly is detected, the atypical parameters of the user's vocal stream are identified and isolated. These isolated parameters are compared with causal indictors for vocal anomalies to identify the most likely cause of the vocal anomaly using a classification model. The vocal anomaly is remedied by automatically triggering notifications about the cause of the vocal anomaly to the appropriate parties. If the classification model cannot define what has caused the vocal anomaly, the user is prompted to input any potential reason they think might have caused the anomaly. This reason, or lack of a reason, is used as feedback into the model for generating more accurate future vocal anomaly classifications.

Often, users will not detect they have expressed an anomaly in their voice in day-to-day conversations, especially if they are verbally expressing themselves for a large part of the day. A slight difference in vocal parameters might seem benign to the person, but with enough frequency or specific combinations of parameters, the variation could be an indicator of a physical or mental health pathology. The vocal anomaly may cause an audience to perceive the communicator incorrectly, but the anomaly may be subtle enough for the communicator not to have noticed the way their vocal information may have been miscommunicated. In one instance, the vocal anomaly could present itself when a speaker makes many calls over a telephone or VoIP network in a single day. For example, the speaker could be attempting to fundraise for a campaign, close a sale, or express some other form of repetitive communication such as a script. The speaker's voice profile could change throughout the day without knowledge of the speaker, and they may accidentally miscommunicate their message due to subtleties they cannot observe. Remedial actions would be deployed or provided in the circumstances where a communication may have been diluted due to the communicator's current state, which they are unaware of.

In another example, a vocal anomaly could be present in the patient of a caregiver in a nursing home environment or hospital who spends a lot of time communicating through digital devices. The patient may speak often, and it would be difficult for a caregiver to detect differences in the patient's voice if they are exposed to the voice often. In some situations, patients may also not be able to express directly a symptom of discomfort to their caregiver. In workplace environments, conditions may prevent individuals from expressing discomfort or less than optimal working environments (e.g. indirectly discouraged by a strict workplace performance culture or management policy, etc.). Additionally, people may have physical or mental disabilities, which make may it difficult for them to express any discomfort or symptoms they are experiencing prior to a diagnosis.

Through a combination of biometric voiceprint generation, an anomaly detection and classification model, and remedial notification generation, one is able to accurately detect, diagnose, and suggest a remedial solution to vocal anomalies detected in long patterns of speech. However, because the biometric voiceprint is specific to an individual speaker, building an accurate model to diagnose individualized speech issues is challenging. For example, when person A is becoming sick with a cold, their voice may become lower in pitch and volume. Person B, however, may express different changes to vocal parameters when experiencing similar symptoms. To correctly diagnose a vocal anomaly and send a remedial notification to the appropriate party, the system can classify the cause of the vocal anomaly by isolating a set of atypical vocal parameters and correlating those parameters with knowledge of causal indicators for vocal anomalies. However, it is a concern that the accuracy of a fixed diagnosis and classification model may degrade as more individuals with unique vocal patterns begin to use the system to diagnose their speech difficulties. Therefore, it would be a significant improvement to existing technologies to allow users to provide feedback about their vocal anomalies to improve the accuracy of future vocal anomaly classifications.

The systems and methods of the present disclosure, in certain embodiments, overcome the limitations of existing solutions by detecting any vocal anomaly through the trained classification model and the biometric voiceprint, and generating an automated response according to the correlation of the atypical parameters with a diagnosis probability. For example, existing solutions may separately diagnose each causation separately, (e.g. diagnosis of a cold with a follow up automated response of changing a schedule of an agent based on the cold, etc.) Additionally, the systems and methods of the present disclosure do not require the input stream of user vocal data to be sent to a remote device for processing, unless a vocal anomaly is detected in the vocal stream. Existing methods typically require an input data stream to be continuously sent to a remote device, because the computational burden of stream analysis and machine learning is too large to perform locally. The systems and methods disclosed herein refer to a remote database in the case that a vocal anomaly is detected, and can perform all threshold comparisons of the user's vocal stream to the biometric profile locally. In some embodiments, the present solution includes a low resolution model that is executed locally, which is capable of comparing the radical anomalous parameters to a matrix of classification values for the individual profile, to give a rough estimate of what the classification could be. In such embodiments, the present solution can send the data to a remote source containing a higher resolution machine learning model responsive to a high enough likelihood of the parameters matching a classification in the value matrix. The remote source can then apply a more accurate and higher definition classification model to the data stream to confirm or deny the classification attempt made by the basic local comparison of the anomalous parameters to the value matrix.

The present solution can automatically generate a biometric voiceprint of a user by receiving pre-recorded vocal samples of the user and combining it with the user's health, personality, and demographics information. The present solution can also generate a biometric profile based off historic data about the user, which can include historic health data and historic changes in their vocal parameters. In some implementations, the present solution gathers the profiling information relevant to generating the biometric voiceprint by providing the user with a questionnaire. The present solution discusses generating a set of vocal parameter thresholds based on the user vocal samples and the profiling data provided by the questionnaire.

The present solution can automatically detect and classify vocal anomalies by comparing a vocal stream with a biometric voiceprint of a user. Automatically classifying a vocal anomaly may result in a misclassification or an inability to diagnose a vocal issue based on vocal fluctuations detected by the device. The present solution discusses systems and methods that can receive manual classification data from the user to improve future classification and identification performance in the future.

In some implementations, the present solution can generate a notification that is associated with a particular classification of a vocal anomaly. For example, during a call, the system may identify, based on a user's speech parameters, that the user is displaying early symptoms of a cold. The present solution would then generate a notification stating that the user may be at risk of becoming ill. The present solution can send the notification containing diagnosis information associated with the user to an appropriate party. For example, if the present solution determines that an employee in a call center is showing signs of becoming ill, then it may send the notification to the manager of the employee to notify the manager of a potential upcoming sick day.

In some implementations, the method includes establishing, by a device, a biometric voiceprint profile of a user and a threshold for a variation range of the user from the biometric voiceprint profile; monitoring, by the device, a vocal stream of the user; detecting, by the device responsive to monitoring, a vocal anomaly based at least on one or more parameters of the vocal stream exceeding the threshold of the variation range of the user from the one or more parameters of the biometric voiceprint profile; identifying, by the device, responsive to the detection, a cause of the vocal anomaly; and communicating, by the device, a notification based at least on the cause of the vocal anomaly.

In come implementations, the biometric voiceprint profile may be established using samples of audio data from the user. In some implementations, the biometric voiceprint profile may be based at least on responses to an assessment to assess health, personality, or demographic information about the user. In some implementations, the method further comprises identifying, by the device using one or more classification techniques, the vocal anomaly from a plurality of vocal anomalies. In some implementations, one or more parameters of the biometric voiceprint profile comprises one or more of the following: highness or lowness of sound, length of time to speak, pitch, volume, tone, duration, rate and inflection. In some implementations, the method further comprises applying a diagnosis model to the one or more parameters to identify a probability of the vocal anomaly.

In some implementations, the method further comprises determining that the probability is greater than a certainty threshold. In some implementations, the method further comprises identifying, in a database having a plurality of notifications, the notification corresponding to the cause of the vocal anomaly. In some implementations, the method further comprises automatically generating a message comprising the notification. In some implementations, the method further comprises detecting, responsive to monitoring, a time period without one or more vocal anomalies and communicating a positive reinforcement message to the user.

In another aspect, the present disclosure is directed to a system for selecting a response based on a cause of a vocal anomaly, the system comprising a device comprising one or more processors, coupled to memory and configured to: establish a biometric voiceprint profile of a user and a threshold for a variation range of the user from the biometric voiceprint profile; monitor a vocal stream of the user; detect, responsive to monitoring, a vocal anomaly based at least on one or more parameters of the vocal stream exceeding the threshold of the variation range of the user from the one or more parameters of the biometric voiceprint profile; identify, responsive to the detection, a cause of the vocal anomaly; and communicate a notification based at least on the cause of the vocal anomaly.

In some implementations, the system is further configured to establish the biometric voiceprint profile using samples of audio data from the user. In some implementations, the system is further configured to establish the biometric voiceprint profile based at least on responses to an assessment to assess one of a health, personality or demographic of the user. In some implementations, the system is further configured to establish a biometric profile based off historic data about the user, which can include historic health data and historic changes in their vocal parameters. In some implementations, the system is further configured to identify, using one or more classification techniques, the vocal anomaly from a plurality of vocal anomalies. In some implementations, one or more parameters of the biometric voiceprint profile comprises one or more of the following: highness or lowness of sound, length of time to speak, pitch, volume, tone, duration, rate and inflection. In some implementations, the device is further configured to apply a diagnosis model to the one or more parameters to identify a probability of the vocal anomaly.

In some implementations, the device is further configured to determine that the probability is greater than a certainty threshold. In some implementations, the device is further configured to identify, in a database having a plurality of notifications, the notification corresponding to the cause of the vocal anomaly. In some implementations, the device is further configured to automatically generate a message comprising the notification. In some implementations, the device is further configured to detect, responsive to monitoring, a time period without one or more vocal anomalies and communicate a positive reinforcement to the user.

The details of various embodiments are set forth in the accompanying drawings and the description below.

BRIEF DESCRIPTION OF THE FIGURES

The foregoing and other objects, aspects, features, and advantages of the present solution will become more apparent and better understood by referring to the following description taken in conjunction with the accompanying drawings, in which.

Figure 1:
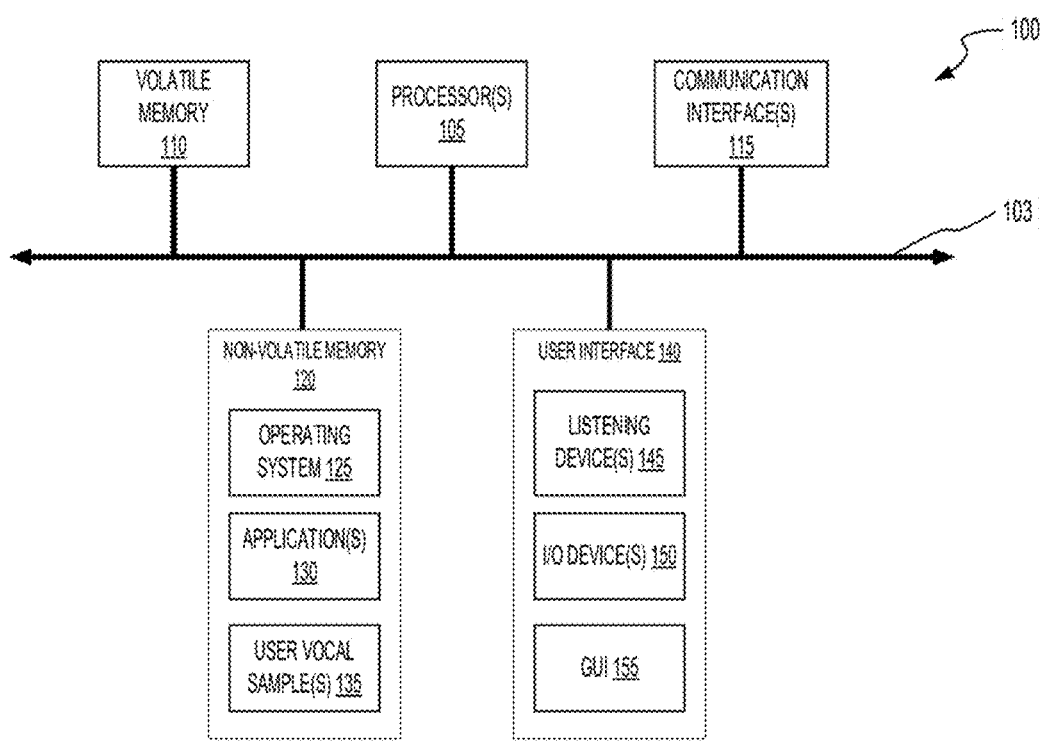
FIG. 1 is a block diagram illustrating an implementation of a network environment for use with the systems and methods discussed herein.

The features and advantages of the present solution will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Prior to discussing the implementations and embodiments of the present solution, it is useful to briefly and general discuss a computing environment on which systems and methods of the present solution may be implemented, performed and/or executed. As shown in FIG. 1, computer 100 may include one or more processors 105, volatile memory 110 (e.g., random access memory (RAM)), non-volatile memory 120 (e.g., one or more hard disk drives (HDDs) or other magnetic or optical storage media, one or more solid state drives (SSDs) such as a flash drive or other solid state storage media, one or more hybrid magnetic and solid state drives, and/or one or more virtual storage volumes, such as a cloud storage, or a combination of such physical storage volumes and virtual storage volumes or arrays thereof), user interface (UI) 140, one or more communications interfaces 115, and communication bus 103. User interface 140 may include one or more listening devices 145 (e.g. a microphone, a webcam, etc.), one or more input/output (I/O) devices 150 (e.g., a mouse, a keyboard, a microphone, one or more speakers, one or more cameras, one or more biometric scanners, one or more environmental sensors, one or more accelerometers, etc.), and a graphical user interface (GUI) 155 (e.g., a touchscreen, a display, etc.). Non-volatile memory 120 stores operating system 125, one or more applications 130, such as the biometric voiceprint profiler 225 of the present solution, and data such that, for example, computer instructions of operating system 125 and/or applications 130 are executed by processor(s) 105 out of volatile memory 110. In some embodiments, non-volatile memory 120 may also contain one or more user vocal samples 135. In some embodiments, volatile memory 110 may include one or more types of RAM and/or a cache memory that may offer a faster response time than a main memory. Data may be entered using an input device of GUI 155 or received from I/O device(s) 150. Various elements of computer 100 may communicate via one or more communication buses, shown as communication bus 103.

Computer 100 as shown in FIG. 1 is shown merely as an example, as clients, servers, intermediary and other networking devices and may be implemented by any computing or processing environment and with any type of machine or set of machines that may have suitable hardware and/or software capable of operating as described herein. Processor(s) 105 may be implemented by one or more programmable processors to execute one or more executable instructions, such as a computer program, to perform the functions of the system. As used herein, the term "processor" describes circuitry that performs a function, an operation, or a sequence of operations. The function, operation, or sequence of operations may be hard coded into the circuitry or soft coded by way of instructions held in a memory device and executed by the circuitry. A "processor" may perform the function, operation, or sequence of operations using digital values and/or using analog signals. In some embodiments, the "processor" can be embodied in one or more application specific integrated circuits (ASICs), microprocessors, digital signal processors (DSPs), graphics processing units (GPUs), microcontrollers, field programmable gate arrays (FPGAs), programmable logic arrays (PLAs), multi-core processors, or general-purpose computers with associated memory. The "processor" may be analog, digital or mixed-signal. In some embodiments, the "processor" may be one or more physical processors or one or more "virtual" (e.g., remotely located or "cloud") processors. A processor including multiple processor cores and/or multiple processors multiple processors may provide functionality for parallel, simultaneous execution of instructions or for parallel, simultaneous execution of one instruction on more than one piece of data.

Communications interfaces 115 may include one or more interfaces to enable computer 100 to access a computer network such as a Local Area Network (LAN), a Wide Area Network (WAN), a Personal Area Network (PAN), or the Internet through a variety of wired and/or wireless or cellular connections.

In described embodiments, the computing device 100 may execute an application on behalf of a user of a client computing device. For example, the computing device 100 may execute a virtual machine, which provides an execution session within which applications execute on behalf of a user or a client computing device, such as a hosted desktop session. The computing device 100 may also execute a terminal services session to provide a hosted desktop environment. The computing device 100 may provide access to a computing environment including one or more of: one or more applications, one or more desktop applications, and one or more desktop sessions in which one or more applications may execute.

Now referring to FIGS. 2-4, details and implementation of the present solution will be discussed. In a general overview, the present disclosure is directed toward detecting and diagnosing vocal anomalies of a user with the intention of providing remedial information. From a vocal anomaly detection perspective, the vocal anomaly may be an irregular highness or lowness of sound. The vocal anomaly may also be an irregular length of speaking time. The vocal anomaly may be an irregular pitch, volume, tone, duration, or speaking rate. The vocal anomaly may be an irregular inflection or affect. Depending on at least the order, frequency, and presence of at least one of the above listed vocal anomalies, the system may choose to generate and send a remedial notification to an appropriate party.

Detection and classification of a vocal anomaly may use a biometric voiceprint profile of a user. The biometric voiceprint profile may include information and vocal parameter thresholds relating to typical patterns of user speech. The present solution establishes a biometric voiceprint of a user prior to the runtime detection of vocal anomalies. The biometric voiceprint profile may include biometric information about the user (e.g. weight, height, etc.) and other information about the user (e.g. personality, health, demographics, etc.). In some implementations, the present solution establishes variation range thresholds for typical variation ranges of vocal parameters using the biometric voiceprint profile. In some implementations, the present solution compares the variation range thresholds to the vocal stream of a user to detect and classify vocal anomalies. The present solution may compare the vocal stream of the user to the biometric voiceprint profile of that user to detect vocal anomalies in real time. When the present solution detects a vocal anomaly, the present solution may send the vocal data to a remote database for later processing. The present solution may use a machine-learning model to detect vocal anomalies in the vocal stream of the user. In some implementations, the present solution detects the vocal anomalies using other methods.

The threshold for typical variation range of the biometric voiceprint profile may be dependent on the user's personality. Differences in personality may indicate that the user may be more prone to a larger profile of dynamic vocal expression. For example, a highly extroverted and excitable user may have a profile with a threshold configured to have a larger margin of error for detecting a vocal anomaly. Users that are highly extroverted or excitable may be more likely to express a more dynamic range of vocal behaviors. In this case, the present solution may configure the biometric voiceprint profile and variation thresholds to accommodate for larger variation to increase the overall accuracy of the system. The present solution detects anomalies in the vocal stream of the user by isolating atypical parameters of the user vocal stream and correlating them with knowledge of causal indicators for vocal anomalies.

Certain implementations, may detect the vocal anomaly when the vocal stream of the user exceeds the variation ranges established using the biometric voiceprint profile. The system and methods may further classify the anomalies by isolating the atypical parameters present in the user vocal stream, and correlating those parameters with knowledge of causal indicators for vocal anomalies. The systems and methods may also classify the vocal anomalies by accessing a remote database containing vocal anomaly information and notification information. Upon classifying the vocal anomaly, the systems and methods may output a diagnosis probability that indicates the probability of the cause of the detected vocal anomaly. In some implementations, the systems and methods may automatically provide a remediation information to the appropriate party related to the diagnosis information. In an example embodiment, a software application is able to monitor the vocal stream of a user via a handheld device or workstation. The biometric voiceprint of the user can be generated, and when a typical threshold of their biometric voiceprint is exceeded, an alert status is sent to a module in the application which then refers to an anomaly detection model to determine what remedial action to take.

In some implementations, remediation information may be an automatic notification. Remediation information may take the form of a notification. The remediation information may take the form of a customized response related to the diagnosis probabilities outputted by the diagnosis model. The remediation information may also take the form of a customized response generated from an existing template response related to the diagnosis probabilities outputted by the diagnosis model. In some implementations, the highest probability of a diagnosis may inform the type of notification (e.g. apology, a follow-up, a notification of state, an alert to an environmental condition, etc.). In some implementations, the highest probability of a diagnosis may inform the appropriate party to which the notification should be sent (e.g. a supervisor, a health specialist, a building manager, the user, the respondent of the user, etc.). In some implementations, the remedial notifications are stored in a database and tagged with a relevant category, and retrieved by the system. The systems and methods may use customer relationship management (CRM) software to communicate with relevant parties outside of the user's network. The systems and methods may use an internal messaging system (e.g. email, instant messaging, etc.) to communicate with the user, management, building managers, or other internal parties.

The systems and methods may flag the user vocal stream with a notification of what the anomaly is. The systems and methods may present a dashboard to a managing party, where all records of user vocal data are stored in a log. In some implementations, responsive to detecting an anomaly, the system may flag the vocal data with an annotation of what the anomaly is in the log. In such implementations, the log may display any anomaly associated with any piece of user vocal data via a label. In some implementations, a manager or supervisor can use the log to monitor anomaly states across many different users, allowing managing parties to monitor the performance of many different users. For example, a supervisor may be able to easily track early symptoms of a cold in certain areas of call center, and take appropriate remedial action. In another example, if parameters associated with a high probability of anxiety were flagged on the dashboard, the managing party would be able to access the call log and identify the trigger for the anxiety.

Figure 2:
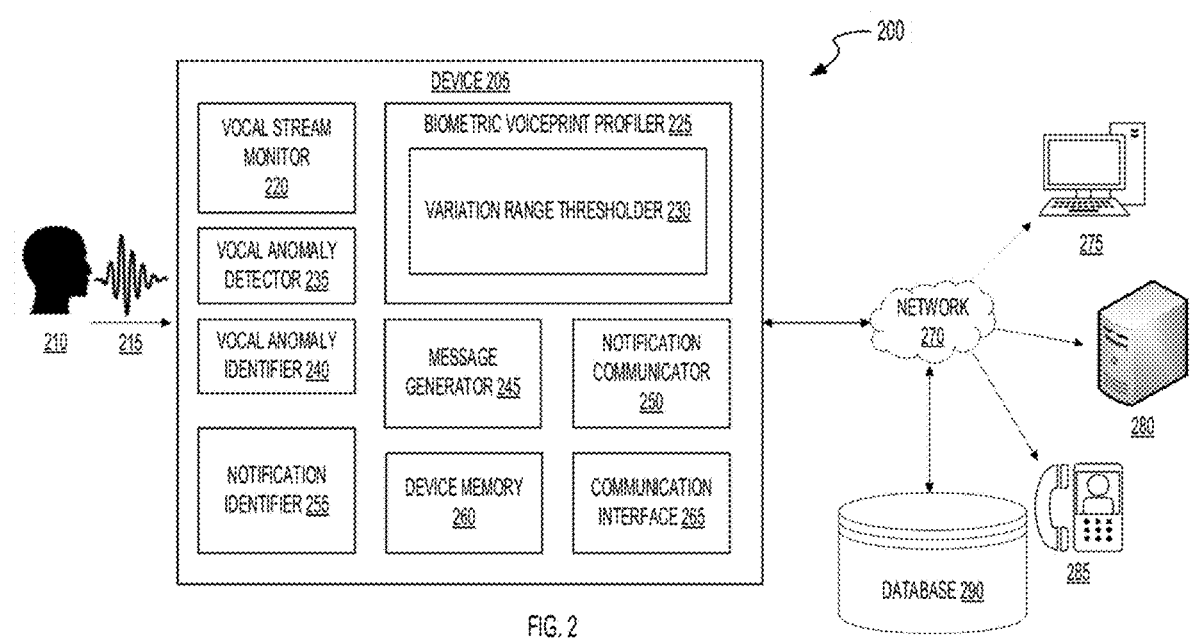
FIG. 2 is a block diagram illustrating an example embodiment of a vocal anomaly detection, classification, and notification system.

For example, FIG. 2 is a block diagram illustrating an example embodiment of a vocal anomaly detection, classification, and notification system 200. In brief overview of FIG. 2, the vocal anomaly detection, classification, and notification system may include a user 210 providing user vocal data 215 to a device 205. The device 205 may also be any device with a microphone, or any device with a speaker and microphone (e.g. a laptop, smart phone, smart watch, headset, gaming console, public switch telephone network (PSTN) landline, desktop PC, etc.). The device 205 can be a computing device 100. The device 205 can execute software implementing the vocal stream monitor 220, the vocal anomaly detector 235, the vocal anomaly identifier 240, the biometric voiceprint profiler 225, the variation range thresholder 230, the notification identifier 255, the message generator 245, and the notification communicator 250. The device 205 can send and receive communication signals (e.g. via voice over internet protocol (VoIP) or public switch telephone network (PSTN), etc.). The vocal anomaly detection, classification, and notification system 200 can include a communication network 270. The communication network 270 can be any type and form of network, including but not limited to an internet protocol (IP) based or a PSTN network. The communication network 270 can send and receive signals originating from device 205, such as audio and/or video signals, for example VoIP communications. The device 205 may communicate with database 290 using the network 270. The device 205 may communicate with any number of notification parties (e.g. computer 275, server 280, or telephone 285, etc.) using the communication network 270.

The device 205 can be any embodiment of computing device 100, described above in connection with FIG. 1, including but not limited to a laptop computer, a desktop computer, a tablet computer, a wearable computer, a smart phone, IP based phone, a conference call system or phone, a smart television, a video game console, a workstation, a server, a smart appliance, a cellular phone, a telephone, a virtual assistant device, headset, or a computer within a vehicle. The device 205 can be any device capable of sending and receiving audio and/or video signals, such as via VoIP or PSTN signals. The device 205 may include any type and form of hardware and software for receiving, detecting or being provide voice or audio as input, such as via a microphone. The device 205 may include any type and form of hardware and software for playing, outputting or providing voice or audio as output, such as via a speaker. The device 205 could be any device that can receive and send audio and microphone inputs via either PSTN or VoIP. For example, the device 205 could be a mobile device belonging to the user. In another example, the device 205 could be a device implemented in a working environment to monitor the voices of employees. In other embodiments, the device 205 is not integrated with a communication system, but is rather used as a microphone that continuously monitors the vocal behavior of the user. For example, the device could monitor face-to-face sales, conference meeting, or day-to-day conversations. In such embodiments, the device 205 may integrate speaker diarisation and background noise reduction to isolate the profile of the user from other audio influences.

Further to FIG. 2, FIG. 2 depicts a user 210 providing user vocal data (e.g. their voice) 215 to the device 205. The user 210 may also be communicating with other parties over the communication network 270, such as via VoIP or PSTN signals using the communication interface 265. The device may have any number of communication interfaces 265. The device 205 can receive the user vocal data 215 and transmit data via the communication network 270. The device 205 can be a single device or multiple devices. The device 205 can detect a vocal anomaly in the user vocal data 215. The device 205 can communicate a notification based on the vocal anomaly to another party over communication network 270. The device 205 can monitor the vocal stream of the user 215 using the vocal stream monitor 220. The device 205 can detect vocal anomalies in the user vocal stream 215 using the vocal anomaly detector 235. The device 205 can identify and diagnose vocal anomalies using the vocal anomaly identifier 240. The device 205 can generate a biometric voiceprint profile using the biometric voiceprint profiler 225. The device 205 can generate variation range thresholds using the variation range thresholder 230. The device 205 may use stored user vocal samples resident in device memory 260 to generate a biometric voice profile using the biometric voiceprint profiler 225. The device 205 may use stored user vocal samples resident in device memory 260 to generate variation range thresholds using the variation range thresholder 230. The device 205 may detect vocal anomalies in user vocal samples resident in device memory 260 using the vocal anomaly detector 235. The device 205 may identify and diagnose a vocal anomaly in user vocal samples resident in device memory 260 using the vocal anomaly identifier 240. The device 205 can identify a notification that is associated with a vocal anomaly diagnosis with the notification identifier 255. Based on the notification, the device 205 can generate a notification message using the message generator 245. The device 205 can communication a notification message using the notification communicator 250 or the communication interface 265. The device 205 may interface to, communicate with or integrate with a database 290 to obtain data and instructions and vocal anomaly information for performing classification and diagnosis of vocal anomalies in user vocal data.

In some implementations, the device 205 can include communication interface 265 and vocal stream monitor 220 for sending and receiving audio-based communications. The communication interface 265 can comprise any combination of hardware and software for communicating, sending or transmitting signals comprising audio content in any type or form. The communication interface 265 can also communicate with any kind of network, including but not limited to an internet protocol (IP) based or a PSTN network. The communication interface 265 can transmit audio signals with audio content using any type and form of protocol, such as VoIP based communications. The communication interface 265 can communicate other information, such as notification information or database information. The communication interface 265 can connect directly or indirectly, by wire or wirelessly to the communication network 270. The communication interface 265 can transmit signals, for example, wirelessly through WiFi or through Bluetooth. The communication interface 265 can be implemented and configured to transmit packets over a network that carry audio content as a payload. The communication interface 265 can be implemented and configured to transmit packets over a network that carry other information, including but not limited to notification information and database information.

The vocal stream monitor 220 can comprise any combination of hardware and software for receiving signals comprising audio content in any type or form. The vocal stream monitor can receive audio signals with audio content using any type and form of protocol, such as VoIP based communications. The vocal stream monitor 220 can connect directly or indirectly, by wire or wirelessly to the communication network 270. The vocal stream monitor 220 can receive signals, for example, wirelessly through WiFi or through Bluetooth. The vocal stream monitor 220 can be implemented and configured to receive and process packets over a network that carry audio content as a payload. The vocal stream monitor 220 may also record and data received by the system and store it on the database 290 or in device memory 260. In some embodiments, the vocal stream monitor 220 may be a software application that is able to monitor the vocal stream of a user via a handheld device or workstation.

The biometric voiceprint profiler 225 can include an application, program, software, scripts, libraries, tasks, services, processors or any type and form of instructions executable on a device, such as for executing biometric voiceprint profile generation and modification. The biometric voiceprint profile may also be called the biometric profile. In some embodiments, the biometric voiceprint profiler 225 can be implemented and configured with logic, functionality, rules or instructions for generating a biometric voiceprint profile in accordance with any of the operations described herein. The biometric voiceprint profiler 225 may also be called a biometric profiler. In some embodiments, the biometric voiceprint profiler 225 (or the voiceprint profiler or biometric profiler as the case may be) carries out any step, function or operation on its own and automatically without user intervention for that step, function or operation.

In some implementations, the biometric voiceprint profiler 225 can be implemented and/or installed and executed on the device 205. In some embodiments, the biometric voiceprint profiler 225 may be stored, installed and executed on a device remote from the device 205, such as being stored and executed on a server, cloud server, a dedicated server or a remote desktop. In some implementations, the biometric voiceprint profiler 225 is stored remotely from device 205 and downloaded, installed and executed from the remote device to the local device 205. In some implementations, the biometric voiceprint profiler 225 is implemented and executed on a network device intermediary to the devices 205 and database 290 such as on a gateway or proxy device.

The biometric voiceprint profiler 225 may access and use the database 290 which may be stored locally on the same device as the biometric voiceprint profiler 225 or stored and accessed over a network on a second device remote to the device of the biometric voiceprint profiler 225. In some implementations, the database 290 can be any type and form of database, relational, object based or otherwise on a server, cloud server, a dedicated server, a remote desktop, or a local computer. In some implementations, the database 290 can comprise multiple databases. The database 290 can be distributed geographically or across multiple database platforms. In some embodiments, the database 290 may comprise a plurality of documents, scripts or files having the information and content described herein. In some embodiments, the biometric voiceprint profiler 225 may obtain updates or changes to the database from another device. In some embodiments, the biometric voiceprint profiler 225 may cache a copy of the database. In some embodiments, the biometric voiceprint profiler 225 use the cache or current copy of the database if the biometric voiceprint profiler 225 does not have access or cannot access a copy or updates of the database from a remote device.

The biometric voiceprint profiler 225 may be designed, configured and/or implemented to generate biometric voiceprint profiles in response to user vocals 215 or audio signals or biometric data. The biometric voiceprint profiler 225 can receive, retrieve, accept, or intercept data packets from a device 205. In some embodiments, the data packets can include data representing or containing audio of conversation(s), such as audio fragments. In some embodiments, the data packets can include data representing or containing biometric information of a user. In some embodiments, the biometric voiceprint profiler 225 can receive, retrieve, or accept biometric information through GUI 155, I/O device(s) 150 or listening device(s) 145. The biometric voiceprint profiler 225 can receive, retrieve, accept, or intercept one or more data packets at a time, such as in real-time, and inspect or analyze the data packet(s) to generate at least one biometric voiceprint profile, such as via using the database 320. Processing the data packets can include identifying the typical parameters of the user's voice. In some embodiments, the data used to generate the biometric voice profile can be samples of voice provided over the run-time mode of the biometric voiceprint profiler 225. Generating the biometric voiceprint profile can also include providing a questionnaire about the user's health, personality, and demographics. The biometric voiceprint profile may be transferred into the vocal anomaly detector 235 and vocal anomaly identifier 240 to correlate diagnosis parameters with history of health conditions for a more accurate diagnosis probability output. In some implementations, the biometric voiceprint profile may be stored locally on the device 205 for privacy reasons and for greater efficiency in executing the comparison with the user vocal data received from vocal stream monitor 220.

The biometric voiceprint profiler 225 may generate the biometric voiceprint of the user based on the typical parameters of their voice and biometric data, including but not limited to vocal samples, health information (e.g. history of heart conditions, asthma, diabetes, etc.), demographic information (e.g. age, sex, height, weight, etc.), and personality information (e.g. extroverted, outgoing, shy, etc.). In some embodiments, the user vocal samples may be provided by repeating a phrase into the listening device(s) 145. In another example, the user vocal samples may be stored on the database 290. In another example, the user vocal samples may be stored in device memory 260 or collected automatically when the user speaks over communication network 270. In some embodiments, the biometric voiceprint profiler 225 may receive biometric information such as health and demographic information by providing a questionnaire to the user on GUI 155. In some embodiments, the biometric voiceprint profiler 225 may receive biometric information from a remote source (e.g. social media accounts, database 290, etc.) over the communication network 270. In some embodiments, the biometric voiceprint profiler 225 may receive personality information from a questionnaire provided to the user through the GUI 155. In some embodiments, the biometric voiceprint profiler 225 may receive personality information from a remote source (e.g. social media accounts, database 290, etc.) over the communication network 270. The vocal parameters considered by the biometric voiceprint profiler may include, but are not limited to highness or lowness of sound, length of time to speak or present an idea, pitch, volume, tone, duration, rate of speech, inflection, and how normal (e.g., happy and healthy) or abnormal the voice may be when compared to historic vocal data or parameter values.

In some implementations, a variation range thresholder 230 can identify or determine, assign or select a typical variation range of user vocal parameters based on the data contained in the generated biometric voiceprint profile. The variation range thresholder 230 can establish a typical variation range for the vocal parameters present in the biometric voice profile. The vocal parameters considered by the variation range thresholder 230 may include but are not limited to highness or lowness of sound, pitch, volume, tone, speech duration, the rate of speech, inflection of speech, and how normal (e.g., happy and healthy) or abnormal the voice may be. In some implementations, the variation range thresholder 230 may also consider personality, health, and demographic information when establishing typical variation ranges for vocal parameters. Health information considered by the variation range thresholder 230 may include but is not limited to a history of heart conditions, asthma, and diabetes. Personality information considered by the variation range thresholder 230 may include but is not limited to information about extroversion, shyness, or excitability. Demographic information considered by the variation range thresholder may include but is not limited to age, sex, height, and weight.

The biometric voiceprint profiler 225 can use, incorporate, integrate, communicate or access the database 290 for configuration, implementation and execution of any of the biometric voiceprint's logic, steps, functions or operations. The database 290 can include user vocal samples, user demographic information, user health information, biometric user profiles, and any other information used by the system 200. In some implementations, the biometric voiceprint profiler 225 may store generated biometric voiceprint profiles locally in device memory 260. In some implementations, the biometric voiceprint profiler 225 may store generated biometric voiceprint profiles remotely in database 290.

The vocal anomaly detector 235 can include an application, program, software, scripts, libraries, tasks, services, processors or any type and form of instructions executable on a device, such as for executing detection of vocal anomalies in vocal streams. In some embodiments, the vocal anomaly detector 235 can be implemented and configured with logic, functionality, rules, or instructions for detecting vocal anomalies in accordance with any of the operations described herein. In some embodiments, the vocal anomaly detector 235 may detect when a vocal stream is free of vocal anomalies. In some embodiments, the vocal anomaly detector 235 carries out any step, function or operation on its own and automatically without user intervention for that step, function or operation.

In some implementations, the vocal anomaly detector 235 can be implemented and/or installed and executed on the device 205. In some embodiments, the vocal anomaly detector 235 may be stored, installed and executed on a device remote from the device 205, such as being stored and executed on a server, cloud server, a dedicated server or a remote desktop. In some implementations, the vocal anomaly detector 235 is stored remotely from device 205 and downloaded, installed and executed from the remote device to the local device 205. In some implementations, the vocal anomaly detector 235 is implemented and executed on a network device intermediary to the device 205, such as on a gateway or proxy device. The vocal anomaly detector 235 may access and use the database 290, which may be stored locally on the same device as the vocal anomaly detector 235 or stored and accessed over a network on a second device remote to the device of the vocal anomaly detector 235. In some embodiments, the vocal anomaly detector 235 may obtain updates or changes to the database from another device. In some embodiments, the vocal anomaly detector 235 may cache a copy of the database. In some embodiments, the vocal anomaly detector 235 use the cache or current copy of the database if the vocal anomaly detector 235 does not have access or cannot access a copy or updates of the database from a remote device.

The vocal anomaly detector 235 may be designed, configured, and/or implemented to detect anomalous fluctuations in the vocal stream of a user. The vocal anomaly detector 235 can receive, retrieve, accept, or intercept data packets from a device 205. The data packets may be raw audio data representing the vocal stream of the user. In some embodiments, the data packets can include typical variation ranges generated from the variation range thresholder 230. In some embodiments, data received by the vocal anomaly detector can include user vocal data, either from the vocal stream monitor 220, the device memory 260, or the database 290. In some embodiments, the vocal anomaly detector 235 can receive packets from communication network 270 containing user vocal samples, variation range thresholds, or biometric user profile information. The vocal anomaly detector 235 can receive, retrieve, accept, or intercept one or more data packets at a time, such as in real-time, and inspect or analyze the data packet(s) to attempt detection of at least one vocal anomaly.

In some implementations, the vocal anomaly detector 235 may use a machine-learning model to detect vocal anomalies. In some implementations, the vocal anomaly detector 235 may use variation range thresholds generated by the variation range thresholder 230 and information from biometric voiceprint profiles to detect vocal anomalies present in user speech. The vocal anomaly detector 235 may detect vocal anomalies in user speech by comparing parameters of the vocal stream with the biometric profile corresponding to the user. In some embodiments, the vocal anomaly detector 235 may detect the absence of vocal anomalies in user speech. In some implementations, the vocal anomaly detector 235 may detect anomalies in user vocal streams by determining if any parameter of the vocal stream exceeds at least one threshold defined by a variation range threshold. In some embodiments, exceeding at least one variation range threshold is considered detection of a vocal anomaly. In some implementations, the vocal anomaly detector 235 forwards the exceeded variation range threshold information, along with biometric voiceprint information and metadata to the vocal anomaly identifier 240 when a vocal anomaly is detected.

The vocal anomaly identifier 240 can include an application, program, software, scripts, libraries, tasks, services, processors or any time and form of instructions executable on a device, such as for classifying and identifying vocal anomalies in vocal streams. In some embodiments, classifying includes diagnosing the reason behind a particular vocal anomaly. In some embodiments, the vocal anomaly identifier 240 can be implemented and configured with logic, functionality, rules, or instructions for identifying vocal anomalies in accordance with any of the operations described herein. In some embodiments, the vocal anomaly identifier 240 may detect when a vocal stream is free of vocal anomalies. In some implementations, the vocal anomaly identifier 240 is unable to identify automatically certain vocal anomalies. In some implementations, the vocal anomaly identifier 240 is able to ask for user input to aid in the identification and classification of vocal anomalies that are not automatically identifiable. In some implementations, manual identification of vocal anomalies results in a more accurate model for future vocal anomaly classifications. In some embodiments, the vocal anomaly identifier 240 carries out any step, function or operation on its own and automatically without user intervention for that step, function or operation.

In some implementations, the vocal anomaly identifier 240 may use a rules based method to diagnose the reason behind a vocal anomaly detected by the vocal anomaly detector 235. In some implementations, the vocal anomaly identifier can use a rules based method to diagnose a cause of a vocal anomaly. In such an implementation, the vocal anomaly identifier 240 compares the variation thresholds exceeded by the vocal stream to known information about certain vocal maladies. In certain embodiments, the vocal anomaly identifier 240 may need a relatively longer amount of audio data to make conclusions about whether or not certain variation thresholds are exceeded. The vocal anomaly identifier 240 may need enough data to compare the real-time vector value of the parameters of the audio data to the typical biometric voiceprint. In such embodiments, the more time the user spends verbally communicating, the more accurate the vocal anomaly identifier 240 will be. These embodiments are most useful where the user is spending a considerable amount of time verbally communicating, for example occupationally or as a social butterfly.

In some implementations, the vocal anomaly identifier 240 contains a low-resolution version of a machine learning classification algorithm that can be run on the device 205. The low-resolution model can be a machine-learning model that is primarily used for classification (e.g., decision trees, logistic regression, rules-based method, random forest, etc.). The vocal anomaly identifier 240 can identify vocal anomalies by comparing the radical anomalous parameters to a matrix of classification values for the individual biometric voiceprint profile generated by the biometric voiceprint profiler 225. In such implementations, the low-resolution model of the vocal anomaly identifier 240 can provide a rough estimate of what the classification of the vocal anomaly could be. If the low-resolution model provides a high enough likelihood of the parameters matching a classification in the value matrix, the vocal anomaly identifier 240 can provide the user vocal data 215, vocal parameters of the user vocal data 215, and associated metadata to a remote source over network 270 using communication interface 265. The remote source can then apply a more accurate and higher definition classification model to the data stream to confirm or deny the classification attempt made by the low-resolution model. The remote source can send the results of the high-resolution classification back to the vocal anomaly identifier 240 over network 270.

In a non-limiting example of a classification scenario, a cold may be associated with a lower than usual pitch, reduced inflection in certain words, and longer pauses between words. If the vocal anomaly identifier 240 determines that a vocal sample, when compared to the ranges established by the variation range thresholder 230, exceeds the same vocal thresholds associated with a cold (e.g. lower pitch, reduced inflection, and longer pauses), the vocal anomaly identifier would output a high probability for the cold diagnosis. Conversely, if the vocal sample, when compared to the threshold established by the variation range thresholder 230, does not exhibit the same exceeded parameters as those associated with the cold, the vocal anomaly identifier 240 will output a low probability for the cold diagnosis. By correlating the exceeded vocal parameter thresholds with a list of possible diagnoses, the vocal anomaly identifier 240 can generate a probability of each possible diagnosis. In certain embodiments, the probability can be outputted based on the prior knowledge of associated vocal attributes and their potential causes. In certain embodiments, changes in biometric data may also factor into the diagnosis of vocal anomalies. For example, increase in weight over a short period, coupled with slower speech, reduced volume, and a more unpleasant or abnormal tone may indicate a diagnosis of depression. In some implementations, database 290 maintains the list of possible diagnoses and their associated parameter thresholds. In some implementations, when the vocal anomaly identifier 240 has diagnosed an anomaly, the vocal anomaly identifier 240 may forward the diagnosis information to the notification identifier 255.

The notification identifier 255 can include an application, program, software, scripts, libraries, tasks, services, processors or any time and form of instructions executable on a device, such as for identifying a notification corresponding to the cause of a vocal anomaly. In some embodiments, identifying the notification includes accessing remote database 290. In some embodiments, the notification identifier 255 can be implemented and configured with logic, functionality, rules, or instructions for identifying vocal anomalies in accordance with any of the operations described herein. In some embodiments, the notification identifier 255 may provide a notification when a vocal anomaly is not detected for a predetermined period. In some embodiments, the notification identifier 255 carries out any step, function or operation on its own and automatically without user intervention for that step, function or operation.

The message generator 245 can include an application, program, software, scripts, libraries, tasks, services, processors or any time and form of instructions executable on a device, such as for generating a message corresponding to the cause of a vocal anomaly. In some embodiments, generating the message includes accessing remote database 290. In some implementations, the message generator receives information from the notification identifier with notification information. In some implementations, pre-written message templates resident on the database 290 or device memory 260 are accessed and populated using information received from the notification identifier 255 responsive to the detection and identification of at least one vocal anomaly. In some embodiments, the information received from the notification identifier includes information about the recipient of the message. In some embodiments, the messages generated by the message generator 245 could be emails, SMS messages, automated phone calls, and push notifications. In some embodiments, the message generator 245 may generate a message if a vocal anomaly is not detected for a predetermined period. In some embodiments, the message may contain protocol information to configure a server responsible for logging vocal anomalies in a user database. In some implementations, the message generator can generate a positive reinforcement message for the user. In some embodiments, the message generator 245 can be implemented and configured with logic, functionality, rules, or instructions for generating messages in accordance with any of the operations described herein. In some embodiments, the message generator 245 carries out any step, function or operation on its own and automatically without user intervention for that step, function or operation.

The notification communicator 250 can include an application, program, software, scripts, libraries, tasks, services, processors or any time and form of instructions executable on a device, such as for communicating a notification or message corresponding to the cause of a vocal anomaly. In some embodiments, communicating the message or notification includes accessing remote database 290. In some implementations, the notification communicator 250 receives a message to communicate from the message generator responsive to receiving detecting at least one vocal anomaly in a vocal stream. In some implementations, the messages are logged in a remote database 290. In some embodiments, the notification communicator 250 interfaces with customer relationship management (CRM) software to provide communication with parties external to the system. In some embodiments, the notification communicator uses an internal messaging system (e.g. email, SMS, instant messaging, etc.) to communicate with parties local to the system. In some embodiments, the notification communicator 250 can communicate a positive reinforcement message to the user. In some embodiments, the notification communicator may update a server or database responsible for logging vocal anomaly events across many users. In some embodiments, the notification communicator 250 carries out any step, function or operation on its own and automatically without user intervention for that step, function or operation.

In a non-limiting example embodiment, device 205 is implemented in a call center environment, where agents are constantly verbally communicating due to occupational requirements. The use cases could also include remote workers whom often communicate over VoIP or landline for their professions and individual sales agents in the field. If an anomaly is detected in a cell center agents' voice, an automated notification can be generated and retrieved from a database of tailored responses, and automatically sent to the relevant party designated by the model. In some embodiments, the database of custom remedial notifications could be stored locally, and may implement customization by the user or the user's employer. In some embodiments, some automatic notifications could be stored on a remote database for universal notifications in all use cases (e.g. if a cold is detected, then a universal response to a user may be "cold symptoms detected, etc."). Depending on the identified case of the anomaly, custom responses would be sent to the designated parties.

Figure 3:
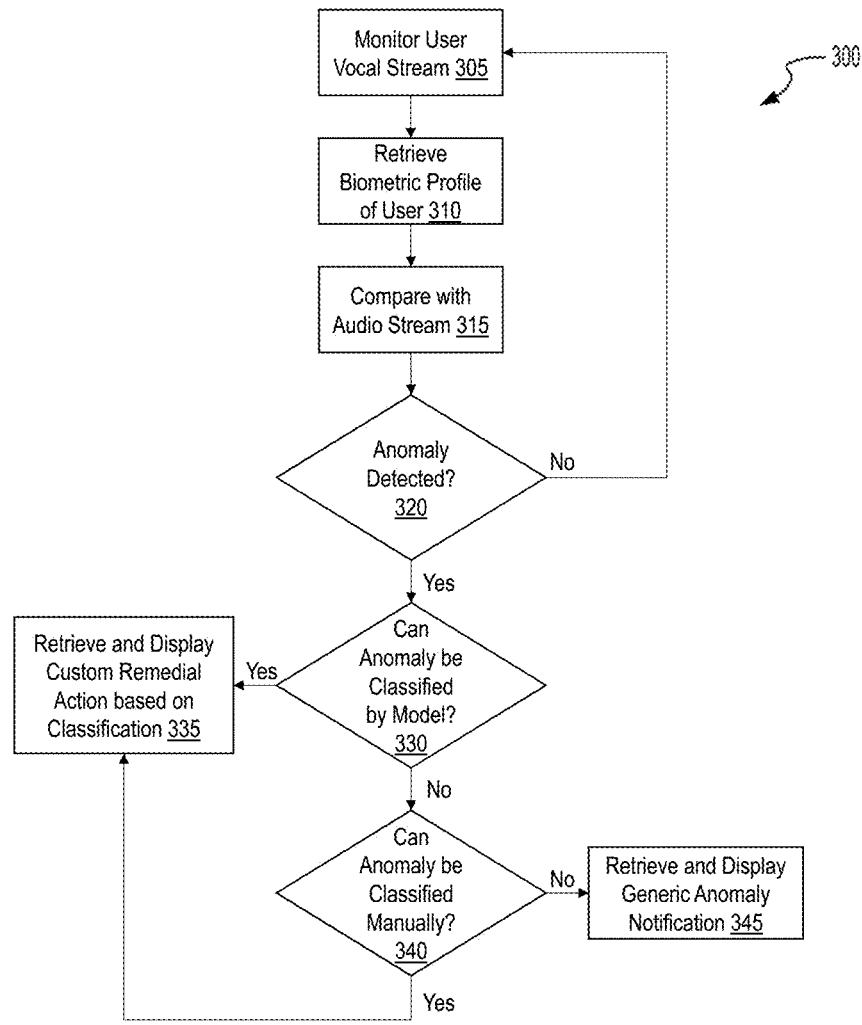
FIG. 3 is a flow diagram illustrating an example embodiment of a method for diagnosing and classifying vocal anomalies in the vocal stream of a user.

FIG. 3 is a flow diagram illustrating an example embodiment of a method for detecting and classifying vocal anomalies in a user, and generating and communicating a notification based on the detected anomaly 300. In brief overview, the method can include user vocal stream monitoring 305, retrieving a biometric profile 310, an audio stream comparison 315, determining if a vocal anomaly is detected 320, determining if the anomaly can be automatically classified 330, retrieving and displaying custom remedial action based on classification 335, determining if the anomaly can be classified manually 340, retrieving and displaying generic anomaly notification 345, and retrieving and displaying custom remedial action based on manual classification 350.

In further details of step 305, continuous monitoring of a user vocal stream occurs. In some embodiments, the vocal stream may be raw audio signals from a listening device such as a microphone, or may be in the form of data packets containing audio data from a user. In some embodiments, the different parameters of the user vocal stream are isolated according to highness or lowness of sound, length of time to speak, pitch, volume, tone, duration, rate and inflection. In some embodiments, the user vocal stream may be from a pre-recorded audio sample from the user. In some embodiments, many audio samples containing user vocals are merged together to create the vocal stream. In some embodiments, logging of the user vocal stream occurs for later processing.

In further detail of step 310, retrieval of the user's biometric profile occurs. The biometric profile of the user can contain thresholds for vocal parameters needed for detection and classification of vocal anomalies. The biometric profile may also contain biometric data that is relevant to the vocal parameter thresholds. For example, vocal thresholds for pitch may be different for males and females. The biometric profile may also contain information about the user's personality. A user who is more extroverted and outgoing may have more dynamic speech patterns than a user who is more introverted and shy. The user who is more outgoing may have larger threshold ranges for vocal activity than the user who is more introverted. The biometric profile may also contain information related to the user's health. For example, individuals with a history of heart disease or smoking may have different vocal thresholds than an individual who does not have a history of heart disease or smoking.

In further detail of step 315, continuous comparisons between the audio stream of the user and the parameters obtained from the user's biometric profile occur. In some embodiments, the vocal parameters compared include but are not limited to highness or lowness of sound, length of time to speak, pitch, volume, tone, duration, rate and inflection. In some embodiments, the vocal parameters of the user's vocal stream are isolated in real-time and compared with the biometric profile thresholds. In some embodiments, comparing the vocal parameters of the user's vocal stream with the parameters contained in the user's biometric profile occurs to detect the presence of vocal anomalies in the user's vocal stream. In some embodiments, comparing the user's vocal stream with the user's biometric profile involves determining if certain parameters of the user's vocal stream exceed thresholds defined by the user's biometric profile. In some embodiments, the thresholds in the user's biometric profile are based on audio samples of the user, the user's health information, the user's personality information, and the user's biometric information. In some embodiments, the thresholds exceeded by the user's vocal stream are isolated and logged.

In further detail of step 320, detection of vocal anomalies in the user's vocal stream occur. In some embodiments, the method detects a vocal anomaly if at least one vocal parameter of the user's vocal stream exceeds at least one threshold contained in the user's biometric profile. In some embodiments, the method can detect more than one vocal anomaly in the user's vocal stream at the same time. In some embodiments, the vocal parameters include but are not limited to highness or lowness of sound, length of time to speak, pitch, volume, tone, duration, rate and inflection. In some embodiments, if the method detects a vocal anomaly in the user's vocal stream, the method isolates the exceeded vocal parameters for classification. In some embodiments, if the method does not detect any vocal anomalies in the user's vocal stream, no remedial actions are performed and the method continues to monitor the user's vocal stream for anomalies. In some embodiments, if the method does not detect any vocal anomalies in the user's vocal stream for a pre-determined period, a positive reinforcement notification is provided to the user. For example, if more than two hours of audio data are returned with no anomalies, the method may provide a reinforcement message stating: "keep up the consistency". Positive reinforcement messages may encourage users to focus on and be aware of how their voice is presented. The method can continue to monitor the vocal data until it detects at least one vocal anomaly in the user's vocal stream. The method can then automatically classify the cause of the one or more vocal anomalies. In some implementations, the method can continue to monitor the vocal data locally without accessing any remote devices (e.g. offline) until a vocal anomaly is detected.

In further detail of step 330, the method attempts to classify automatically at least one vocal anomaly in the user's vocal stream to determine the cause of the one or more vocal anomalies. In some embodiments, the method classifies vocal anomalies in the user's vocal stream using a machine-learning method. The method may access a remote computing resource, such as a cloud computing service or on a local server to access a diagnosis and classification model. In some embodiments, the method may retrieve the diagnosis and classification model and apply it to the anomaly parameters. In some embodiments, the method classifies vocal anomalies in the user's vocal stream using a rules based model. The method can correlate a list of possible diagnoses and their associated rules (e.g. exceeded thresholds) with the thresholds exceeded by the user's vocal stream. The method can assign the items in the list of diagnoses that most closely match the thresholds exceeded by the user's vocal stream the highest probability of diagnosis, while the method assigns the items in the list of diagnoses that least closely match the thresholds exceeded by the user's vocal stream the lowest probability of diagnosis. In some embodiments, the rules based model outputs a list of probabilities, with each probability associated with a diagnosis. The method can perform a soft-max operation to choose the diagnosis that most closely matches the vocal anomalies detected in the user's vocal stream. In some other embodiments, the method will choose the diagnosis with a probability that exceeds a pre-determined threshold. In some embodiments, the method can use a low resolution model that is executed locally, which is capable of comparing the radical anomalous parameters to a matrix of classification values for the individual profile, to give a rough estimate of what the classification could be. In such embodiments, the method can send the data to a remote source containing a higher resolution machine learning model responsive to a high enough likelihood of the parameters matching a classification in the value matrix. The remote source can then apply a more accurate and higher definition classification model to the user vocal data stream to confirm or deny the classification attempt made by the basic local comparison of the anomalous parameters to the value matrix. The method may fetch a corresponding remedial notification responsive to choosing a diagnosis corresponding to a vocal anomaly. In some embodiments, the method may be unable to classify appropriate party. The custom remedial notification may be sent via CRM software when, for example, notifications should be sent automatically to a customer. In some embodiments, the custom remedial action may include logging the vocal anomaly diagnosis associated with a particular user in a database or memory storage. Non-limiting examples of diagnoses and their associated remedial notifications are included in the table below:

| Cause of anomaly | Remedial Action/s |
| --- | --- |
| Early symptoms of cold/virus or allergies | Notify agent & manager/supervisor of potential upcoming sick days, notify customer of potential up- coming change in account manager or ticket solver |
| Heavy symptoms of cold/virus | Notify customer/communication respondent of state of the agent so they understand why they might have been different, notification for health professionals. Notification to route calls to a different agent. |
| Fatigue | Notify manager/supervisor to keep an eye on workload/schedule. Notify agent to take remedial action i.e. take a break, have fresh air, do some stretches, notify respondent of potential error and follow-up if fatigue is high enough. If fatigue is frequent then notifications for dietary remedies. |
| Motivational reasons/burnout signs | Notify supervisor/manager to look into motivational issues to inform management strategies |
| Mental health reasons, i.e. depression or anxiety | Notify specialist, notify agent of potential changes to increase self-awareness of their mental states, notify management |
| Connection/infrastructure affecting the quality of the call | Notify building manager or office manager of potential connection issues, automatically send apology to customer as follow-up for poor connection quality |
| Environmental Reasons i.e. suboptimal oxygen or co2 levels, temperature, pollutants in air, dust or mold etc | Notification to change the air quality to building manager or to management, notification to agent to open a window to let in more fresh air. |
| Weight changes | Notification to the agent for potential dietary recommendations, if the weight changes are also correlated with high chances of fatigue or motivational reasons then notify management or specialist as to other possible symptoms associated with the weight changes. | automatically the cause of the one or more vocal anomalies detected in the user's vocal stream.

In further details of step 335, the method performs a custom remedial action based on the automatic classification in step 330. Remedial actions may be customized responses to the diagnosis probabilities outputted from the diagnosis model. The highest probability of diagnosis may inform what type of notification needs to be sent (e.g., an apology, a follow-up, a notification of a state, an alert to change an environmental condition) and who the notification should be sent to (e.g. a supervisor, a health specialist, a building manager, the user, the respondent of the user). In some embodiments, the remedial notifications may be stored in a database and tagged with a relevant category. The method may access the database to retrieve the remedial notification responsive to the output probability of the diagnosis model is higher than a sufficient probability threshold, for example 90 percent. The sufficient probability threshold may be customized dependent on the use case, but the first iterations would be quite high as the diagnosis model may not be as optimized as it would be after processing more data, for example many hours. The sufficient probability threshold may also be called the certainty threshold. In some embodiments, the remedial action is to send a notification to an appropriate party. For example, the method may notify a customer that the infrastructure of the call was having issues, and may provide an incentive offer for the inconvenience. In some embodiments, the custom remedial action may be to generate an email, SMS, or instant message to send to an In further details of step 340, in the event that the method cannot automatically classify the diagnosis for the one or more vocal anomalies detected in the user vocal stream, the method prompts the user for a manual classification of the one or more vocal anomalies. The method may generate a notification for the user detailing the vocal anomalies to the user and asking for a manual diagnosis. The user may input a state or symptom they think they could be experiencing. The method can use the manual classification as training data to improve the accuracy of the classification and diagnosis model. For example, if the user believes they are experiencing the early symptoms of a cold, then this information would be used to further train the classification and diagnosis model. In some embodiments, the user may manually classify that there was no vocal anomaly diagnosis during the detected period. For example, the user may have no obvious symptoms or awareness of why an anomaly may have been detected. Manual classifications of the absence of a vocal anomaly can be used as feedback training data to improve the accuracy of the of the classification and diagnosis model. The method may retrieve a remedial notification responsive to the manual classification of the vocal anomaly. In some embodiments, the user may be unable to classify manually the vocal anomaly.

For example, in the first iterations of the classification and diagnosis model, the parameters correlated to a diagnosis could be provided from prior knowledge of vocal related diagnoses. There exist medical machine learning diagnostics that can detect the early signs of cancers, and the onset of a cold or flu. The classification and diagnosis model may apply the features in such medical machine learning diagnostic models. For example, if vocal thresholds have been exceeded, and the parameters that have contributed to the threshold being exceeded are isolated, then a rules based method can be implemented to diagnose the anomaly. Certain diagnoses may have shared parameters, for example fatigue and early signs of a cold. The first iterations of the classification and diagnosis model may not be able to differentiate those diagnoses without additional input training data. In this example, further iterations of the model will be able to detect complex diagnoses that may use additional data points to differentiate similar symptoms. These additional data points may be gathered from the manual classifications provided by the user. In some embodiments, the manual classifications may occur when an anomaly has no known correlation or when there is a conflict in the diagnosis (e.g. the probability for multiple diagnoses are the same).

In further details of step 345, in the event that the user cannot manually classify the diagnosis for the one or more vocal anomalies detected in the vocal stream, the method will retrieve a generic anomaly notification. For example, the method may detect one or more vocal anomalies in a user's vocal stream, but is unable to make an automatic classification. The method prompts the users to make a manual classification, but the user is unable to classify the vocal anomaly. The method then retrieves a generic anomaly notification from a database or other notification storage. For example, in a call center environment, the method may send "an agent has expressed a high probability of an anomaly but there is no classification," to the supervisor of the call center. Furthering this example, the generic notification may be sent to a customer as a follow-up in cases where the vocal anomaly was extreme and most likely obvious to the customer. In some embodiments, the retrieved notification may be associated with the user. The retrieved notification may be associated with the user's vocal stream. In some embodiments, the method may log the retrieved notification to a server or other vocal anomaly database or storage.

Figure 4:
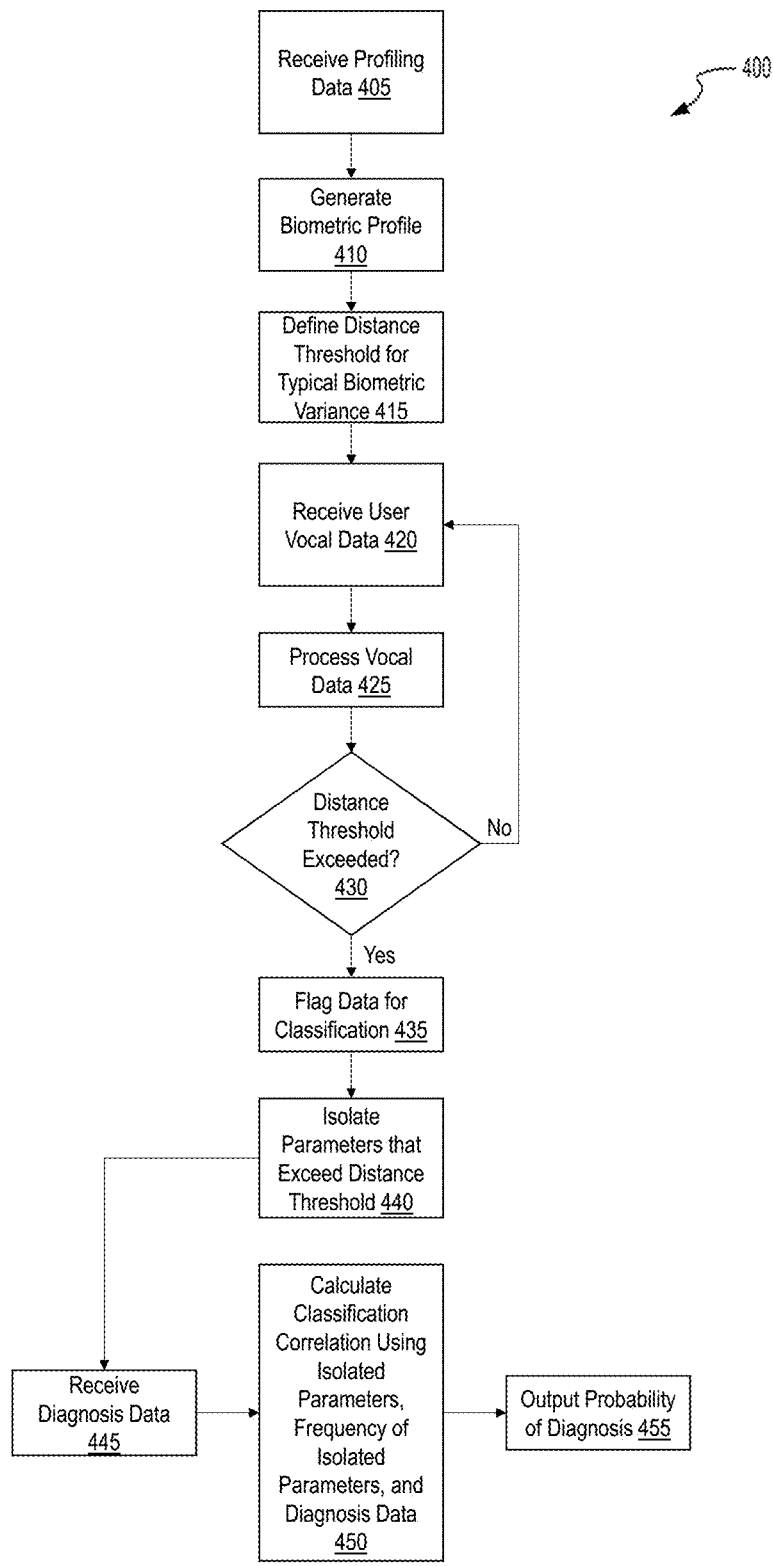
FIG. 4 is a flow diagram illustrating an example embodiment of a method for generating and using a biometric profile to classify vocal data.

FIG. 4 is a flow diagram illustrating an example embodiment of a method 400 for generating a biometric profile and classifying a diagnosis based on vocal parameters. In brief overview, the method 400 can receive profiling data 405, generate a biometric profile 410, define a distance threshold for typical biometric variance 415, receive user vocal data 420, process vocal data 425, check if the distance thresholds defined in 415 are exceeded 430, flag data for classification 435, isolate parameters that exceed distance threshold 440, receive diagnosis data 445, calculate classification correlation using isolated parameters, frequency of isolated parameters, and diagnosis data 450, and output a probability of a diagnosis 455.

At step 405, the method receives profiling data from the user with the intention of using the profiling data to generate a biometric profile for the user. In some embodiments, the profiling data can contain information about the health of the user. For example, the profiling data may contain information about a history of heart attacks, smoking, or diabetes. In some embodiments, the profiling data may contain information from the user relating to the user's personality. For example, the profiling information may contain information about the user's tendency to be outgoing or excitable. In some embodiments, the profiling data may contain biometric information about the user. For example, the profiling data may contain information about the user's age, sex, weight, or height. In some implementations, the profiling data may include demographic information about the user. In some implementations, the profiling data may also include pre-recorded audio samples from the user. In some embodiments, the method may receive the profiling data from an external database or storage medium containing information from at least one user. The profiling data may include metadata about the user, and may include responses to surveys. Metadata may include responses to surveys and/or a form for the user to complete. The profiling data may include the metadata. In some embodiments, the method may receive the profiling data from the user through an assessment, questionnaire, or questionnaires. In some embodiments, during the setup phase, the method may provide a questionnaire or assessment to assess the user's health, personality, and demographics. The questionnaire may be similar to what a doctor would present at first checkup. For example, the questionnaire may include questions about a history of heart conditions, asthma, or diabetes. The questionnaire may also include questions about the user's demographics (e.g. age, sex, height, weight). The questionnaire may include personality information about the user. The method may gather vocal samples of the user by prompting the user to repeat one or more phrases, for example into a microphone, until a profile can be generated. In some implementations, run-time data may be gathered during run-time after the initial biometric profile is generated, in order to fine-tune the biometric profile. In some embodiments, the method may establish the biometric voiceprint profile based on the one or more assessments or questionnaires.

At step 410, the method generates a biometric profile for a user using the profiling data received at step 405. Generating the biometric profile for the user can be similar to generating a voiceprint for security or vocal identification purposes. In some embodiments, creating a user's biometric profile involves extracting vocal parameters from audio samples of the user obtained in step 405. The biometric profile of the user may be generated based on typical parameters of the user's voice. The vocal parameters may include but are not limited to highness or lowness of sound, length of time to speak, pitch, volume, tone, duration, rate and inflection. In some embodiments, the method may base a user's biometric profile on the user's health information, personality information, or demographic information obtained in step 405. In some embodiments, the method may base a user's biometric profile on the user's health information, personality information, and/or demographic information obtained from one or more assessments or questionnaires. Generating the biometric profile may include processing the pre-recorded user vocal samples into spectrograms based on the parameters of the vocal samples. Step 410 may also include inputting data associated with the biometric profile (e.g., health, demographics, personality, vocal samples) into a diagnostic model to correlate diagnosis parameters with history of health conditions for more accurate diagnosis probability output. In some implementations, the data used to generate the vocal profile can be samples of voice provided over the run-time mode of the method. The personality testing may be used for configuring a threshold for typical behavior of the biometric voiceprint.

At step 415, the method establishes distance thresholds for typical biometric variance for one or more vocal parameters. In some embodiments, the typical biometric variance is influenced by the results of a user questionnaire provided in step 405, and other metadata gathered in step 405. The method may base the typical biometric variance on the profiling data received in step 405 and the biometric profile generated in step 410. The method may also establish the distance thresholds to account for the personality information included in the biometric profile. The personality information may be used for configuring the threshold for typical behavior of the biometric voiceprint. For example, a highly extroverted, excitable person would have a profile with a threshold configured to have a larger margin of error for detecting an anomaly, as they are more likely to express a more dynamic range of vocal behaviors that may not necessarily be indicative of an anomaly. Different demographics, for example age, may also contribute to typical biometric variation. The distance thresholds may also depend on the typical variation range in every day vocal samples, or on the user's proneness to erratic fluctuations. In some embodiments, the method configures the variation distance thresholds based on the overall accuracy of the diagnosis and classification model. In such embodiments, in the first iterations while the method is training the model, the method may increase the threshold so that fewer false classifications occur due to a less accurate model. In some implementations, the more inputs the model receives during run mode, the more confidence the model will have in outputting a diagnosis. In such implementations, with the greater confidence in the model, the thresholds can be reduced. The thresholds may also be determined by typical variance of the profile of the user in day-to-day voice samples. The method may calculate the variance thresholds using a machine-learning algorithm, for example a logistic regression or unsupervised clustering of data points.

The method may classify user vocal data, in some embodiments responsive to establishing difference thresholds. The method may need to calculate the distance thresholds for typical biometric variance once before the method can classify user vocal data. The method may store the thresholds for biometric variance data in a local storage medium. The method may also store the thresholds for biometric variance in a remote location. The method may update the distance thresholds for biometric variance in response to new user data or vocal data. If the method has already established the distance thresholds for typical biometric variance, the method can skip to step 420 to begin classifying user vocal data in real-time. The method may attempt to retrieve the variance thresholds from a remote location before attempting to establish them locally.

At step 420, the method receives user vocal data to process using a classification model. In some embodiments, the method can receive the user vocal data from a microphone into which the user is speaking. The method can receive the user vocal data from audio files containing pre-recorded audio data from the user. The method may receive the user vocal data from an external database or internal storage. Receiving the vocal data may also include applying additional speaker diarisation and background noise reduction to isolate the user from other audible interference.

At step 425, the method processes the user vocal data received in step 420. In some embodiments, the method may process the user vocal data into a variety of spectrograms to isolate certain vocal parameters. In some implementations, the method may process the user vocal data for comparison to the distance thresholds established in step 415. In some implementations, the method may analyze the user vocal data to isolate certain vocal parameters. In some implementations, the isolated vocal parameters may include but are not limited to highness or lowness of sound, length of time to speak, pitch, volume, tone, duration, rate and inflection.

At step 430, the method may compare the vocal data processed in step 425 to the distance thresholds calculated in step 425. For example, the method can determine if there is an additional classification step by checking if any of the vocal parameters isolated in step 430 exceed any of the distance thresholds established in step 415. If any of the vocal parameters exceed the distance thresholds, then the method has detected at least one vocal anomaly in the speech of the user to further classify. The method can return to step 420 if there is no anomaly detected in the user speech, allowing the method to monitor continuously user speech until detection of a vocal anomaly.

At step 435, the method flags a sample of the user's voice for further classification when any of the vocal parameters isolated in step 425 exceed the thresholds established in step 415. The vocal sample that is flagged will be processed further to classify and diagnose the cause of the vocal anomaly (e.g. exceeded thresholds) observed by the method. In some embodiments, more than one vocal parameter may exceed more than one threshold established in step 415. The method may associate the flagged vocal samples with a particular user. The method may also associate the flagged vocal samples with data in the user's biometric profile. In some embodiments, the method may duplicate or save flagged vocal samples to a local storage location. The method may also duplicate or save flagged vocal samples to a remote storage location.

At step 440, the parameters that exceeded the distance thresholds in step 430 are isolated based on the audio data flagged in step 435. If the method established the biometric profile and variance thresholds with an unsupervised clustering model, the method can isolate the vocal parameters by analyzing the output coordinates of the vector. If the method established the biometric profile and variance thresholds with a logistic regression model, defining the isolated parameters would implement an additional step of statistical analysis to extract the features that determine the one or more vocal anomalies.

At step 445, the method retrieves diagnosis data to prepare to classify further the vocal parameter data that was isolated in step 440. In some implementations, the diagnosis data could correspond to the potential diagnoses related to the types of vocal parameters isolated in step 440. For example, if the vocal parameters isolated in step 440 included a higher pitch, long pauses between words, and less intonation for words, then the method would retrieve any diagnosis data that relates to those parameters. In some implementations, the retrieved diagnosis data may also include the profiling data gathered in step 405. In some embodiments, the diagnosis data may include a list of possible diagnoses related to the parameters isolated in step 440. Diagnosis data may also include user metadata and profiling data. In some implementations, the diagnosis data is contained in an external database.

At step 450, the method correlates the diagnosis data retrieved in step 445 to the parameters isolated in step 440 to generate correlations for each of the possible diagnoses included in the diagnosis data. For example, if the vocal parameters isolated in step 440 correlate strongly to the features of a particular diagnosis, then the method will assign the diagnosis a high probability. Conversely, if the vocal parameters correlate poorly to the features of a particular diagnosis, then the method will assign the diagnosis a low probability. In some implementations, the method factors the frequency of the isolated parameters into the correlation of the isolated parameters and the diagnosis data. In some implementations, if the method cannot perform automatic classification, the method asks the user to perform a manual classification of the data. In such an implementation, the method uses the manual input as a classification tag for the isolated parameters isolated in step 440. In some implementations, in the first iterations the diagnosis data will include set parameters, which are known to be correlated with a diagnosis (e.g. higher pitch, longer pauses between words, and less intonations means a high probability of a cold).

At step 455, the method outputs a probability of a diagnosis. In some implementations, the method can take the correlations calculated in step 450 and place them into a soft-max layer. In some implementations, the soft-max layer distributes the probabilities of the isolated parameters with the diagnosis data and frequency of isolated parameters. The probability distribution can give an output of a likelihood of a diagnostic classification of the inputs across multiple diagnoses. For example, if the model has the following inputs for diagnosis data: cold, fatigue, air quality, anxiety, and depression, then the method assigns each of those diagnoses a value based on the probability that it is the correct classification. The method outputs the diagnosis that has the greatest probability. In some implementations, the method outputs a diagnosis and the likelihood (e.g. probability) associated with the diagnosis to establish a known level of confidence in the result produced by the model. For example, if the model has a five input diagnostic criteria: cold, fatigue, air quality, anxiety, and depression, then the method would assign each classification a value based on the probability that it is the correct classification. This output probability of the diagnosis is the output of the entire model.

A non-limiting example embodiment of the systems and methods of this disclosure is described herein. In this example, vocal data is collected from employees working remotely for large enterprise or for call centers. These employees are responsible for customer service, sales, or support. Voice data is matched with each individual employee, and is labeled and stored in a database system. From this data, a biometric profile is created for each employee. In this non-limiting example, the factors included in the biometric profile are: highness or lowness of sound on a scale, length of time to speak or present, pitch, volume, tone, duration, rate of speech, inflection, normality (e.g., happy and healthy), and web tracking data. Each call made by the employees is recorded, labeled, and saved in a database system in order to enhance the biometric profile of each employee over time. After a pre-determined number of hours, a detailed biometric profile is created, and the anomaly detection algorithm is initiated. The machine-learning based algorithm looks at the user profile averages after each call, and checks if any anomalies occurred after the call has been completed. If any anomalies were detected, a message is presented to the user to remediate the issue that has been detected. If the anomaly threshold has been surpassed by a pre-determined amount, an automatically generated alert is sent to both the customer and the supervisor.

For the purposes of furthering the non-limiting example above, an implementation of a customer notification template is included below:

---

Hello < Name from CRM >,
We saw that you had a call with < Employee Name > and wanted to make sure everything was satisfactory on your end. If there were any problems, please email us directly using this link < Link > or please call me directly at < Phone Number >.
  Regards,
    < Supervisor Name >

---

For the purposes of furthering the non-limiting example above, an implementation of a supervisor notification template is included below:

---

Hey < Supervisor Name >,
< Employee Name > had an unpleasant call and the main reason for this was < Diagnosis Information >. We have alerted the customer to maintain our level of integrity to providing the best service.
  Best,
    < Service Name >

---

It should be noted that certain passages of this disclosure may reference terms such as "first" and "second" in connection participants, users, devices, accents, dialects, contexts, etc., for purposes of identifying or differentiating one from another or from others. These terms are not intended to merely relate entities (e.g., a first device and a second device) temporally or according to a sequence, although in some cases, these entities may include such a relationship. Nor do these terms limit the number of possible entities (e.g., devices) that may operate within a system or environment.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a hard disk, a CD-ROM, a flash memory card, a PROM, a RAM, a ROM, or a magnetic tape. In general, the computer-readable programs may be implemented in any programming language, such as LISP, PERL, C, C++, C #, PROLOG, or in any byte code language such as JAVA. The software programs or executable instructions may be stored on or in one or more articles of manufacture as object code.

While the foregoing written description of the methods and systems enables one of ordinary skill to make and use what is considered presently to be the best mode thereof, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C #, PROLOG, or in any byte code language such as JAVA. The software programs may be stored on or in one or more articles of manufacture as object code.

While various embodiments of the methods and systems have been described, these embodiments are illustrative and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the illustrative embodiments and should be defined in accordance with the accompanying claims and their equivalents.

The invention claimed is:

1. A method for selecting a response based on a cause of a vocal anomaly, the method comprising:
   generating, by a device, a biometric voiceprint profile of a user, the biometric voiceprint profile comprising a plurality of vocal parameters relating to a voice of the user;
   determining, by the device, a threshold variation range of each vocal parameter of the plurality of vocal parameters included in the biometric voiceprint profile;
   monitoring, by the device, a vocal stream of the user by extracting a second plurality of vocal parameters from the vocal stream;
   detecting, by the device responsive to monitoring the vocal stream, a vocal anomaly based at least on a second vocal parameter of the second plurality of vocal parameters of the vocal stream exceeding the threshold variation range of a corresponding vocal parameter of the biometric voiceprint profile of the user;
   identifying, by the device, responsive to detecting the vocal anomaly, a cause of the vocal anomaly based on the second vocal parameter that exceeded the threshold variation range of the corresponding vocal parameter of the biometric voiceprint profile; and
   communicating, by the device, a notification based at least on the cause of the vocal anomaly.

2. The method of claim 1, wherein generating the biometric voiceprint profile is further based on samples of audio data from the user.

3. The method of claim 1, determining the threshold variation range of each vocal parameter is further based on one or more responses to an assessment to assess one of a health, personality or demographic of the user.

4. The method of claim 1, further comprising identifying, by the device using one or more classification techniques, the vocal anomaly from a plurality of vocal anomalies.

5. The method of claim 1, wherein the plurality of vocal parameters of the biometric voiceprint profile comprises one or more of the following: highness or lowness of sound, length of time to speak, pitch, volume, tone, duration, rate and inflection.

6. The method of claim 1, further comprising applying a diagnosis model to the second plurality of vocal parameters extracted from the vocal stream to identify a probability of the vocal anomaly.

7. The method of claim 6, further comprising determining that the probability is greater than a certainty threshold.

8. The method of claim 1, further comprising identifying, in a database having a plurality of notifications, the notification corresponding to the cause of the vocal anomaly.

9. The method of claim 8, further comprising automatically generating a message comprising the notification.

10. The method of claim 1, further comprising detecting, responsive to monitoring the vocal stream, a time period without one or more vocal anomalies and communicating a positive reinforcement message to the user.

11. A system for selecting a response based on a cause of a vocal anomaly, the system comprising:
    a device comprising one or more processors, coupled to memory and configured to:
        generate a biometric voiceprint profile of a user, the biometric voiceprint profile comprising a plurality of vocal parameters relating to a voice of the user;
        determine a threshold variation range of each vocal parameter of the plurality of vocal parameters included in the biometric voiceprint profile;
        monitor a vocal stream of the user by extracting a second plurality of vocal parameters from the vocal stream;
        detect, responsive to monitoring the vocal stream, a vocal anomaly based at least on a second vocal parameter of the second plurality of vocal parameters of the vocal stream exceeding the threshold variation range of a corresponding vocal parameter the biometric voiceprint profile of the user;
        identify, responsive to detecting the vocal anomaly, a cause of the vocal anomaly based on the second vocal parameter that exceeded the threshold variation range of the corresponding vocal parameter of the biometric voiceprint profile; and
        communicate a notification based at least on the cause of the vocal anomaly.

12. The system of claim 11, wherein the device is further configured to generate the biometric voiceprint profile based on samples of audio data from the user.

13. The system of claim 11, wherein the device is further configured to determine the threshold variation range of each vocal parameter based on one or more responses to an assessment to assess one of a health, personality or demographic of the user.

14. The system of claim 11, wherein the device is further configured to identify, using one or more classification techniques, the vocal anomaly from a plurality of vocal anomalies.

15. The system of claim 11, wherein the plurality of vocal parameters of the biometric voiceprint profile comprises one or more of the following:
    highness or lowness of sound, length of time to speak, pitch, volume, tone, duration, rate and inflection.

16. The system of claim 11, wherein the device is further configured to apply a diagnosis model to the second plurality of vocal parameters to identify a probability of the vocal anomaly.

17. The system of claim 16, wherein the device is further configured to determine that the probability is greater than a certainty threshold.

18. The system of claim 11, wherein the device is further configured to identify, in a database having a plurality of notifications, the notification corresponding to the cause of the vocal anomaly.

19. The system of claim 18, wherein the device is further configured to automatically generate a message comprising the notification.

20. The system of claim 11, wherein the device is further configured to detect, responsive to monitoring the vocal stream, a time period without one or more vocal anomalies and communicate a positive reinforcement message to the user.

* * * * *